US006251953B1

(12) United States Patent
Baranowitz

(10) Patent No.: US 6,251,953 B1
(45) Date of Patent: Jun. 26, 2001

(54) BETA-CAROTENE THERAPY OF INDIVIDUALS HAVING ABNORMAL IMMUNOLOGICAL AND SEROLOGICAL INDICES, AND INDIVIDUALS HAVING INFECTIONS AND DISEASES CAUSING CHANGES THEREIN

(75) Inventor: Steven Baranowitz, East Brunswick, NJ (US)

(73) Assignee: Andrew Brookner, Short HIlls, NJ (US)

( * ) Notice: Subject to any disclaimer, the term of this patent is extended or adjusted under 35 U.S.C. 154(b) by 0 days.

(21) Appl. No.: 08/320,557

(22) Filed: Oct. 11, 1994

Related U.S. Application Data

(63) Continuation of application No. 07/969,485, filed on Oct. 30, 1992, now abandoned.

(51) Int. Cl.$^7$ .................... A01N 27/00; A61K 32/015
(52) U.S. Cl. .................................... 514/764; 514/765
(58) Field of Search ............................ 514/764, 765

(56) References Cited

U.S. PATENT DOCUMENTS

| | | |
|---|---|---|
| 4,983,637 | 1/1991 | Herman . |
| 5,086,076 | 2/1992 | Herman . |
| 5,126,376 | 6/1992 | Herman . |

OTHER PUBLICATIONS

Loya et al 116 CA: 98949c 1992.*
Seifter et al 97 CA:54415k 1982.*
Desjonqueres 107 CA:205197u 1987.*
Mascioli et al 104 CA: 230488k 1986.*
Bendich 116 CA: 104875u 1992.*
Harrison et al J Medical Virology 32 128–32 1990 See 081814099.*
Alexander et al 113 CA: 184708t 1990.*
Bendich, A. *Proc. of the Nutrition Society* 50:263–274, 1991.
Bianchi, L. et al., *Anticancer Research* 13:1007–1010, 1993.
Umegaki, K. et al., *Am. J. Clin. Nutr.* 59:409–12, 1994.
Hutterer et al., *J. Infect. Dis. J.*, 165:783–784, Apr., 1992.
Ellaurie et al., *Ped. Infect. Dis. J.*, 11:4, 286–289, Apr., 1992.
Jacobson et al., *Brit. Med. J.*, 302:73–78, Jan. 12, 1991.
Muller et al., *Clinica Chimica Acta*, 201:1–16 (1991).
Keller et al., *Cells of the Hepatic Sinusoid*, 3:414–416 (1991).
Polis et al., *Am. J. Med.*, 89:701–704, Dec., 1990.
Harrison et al., *J. Med. Vir.*, 32:128–133, 1990.
Fuchs et al., *Clin. Chem.*, 35:8, 1746–1749, 1989.
Alexander et al., *Immunology Letters*, 9:221–224, 1985.
Ringer et al., *Am. J. Clin. Nutr.*, 53:688–694, 1991.
Kanofsky et al., *Med. Trib.*, 26–31, Apr. 22, 1987.
Watson et al., *Life Sci.*, 43:XIII–XVIII, 1988.
Nashima et al., *Med. Microbiol. Immunol.*, 176:189–198, 1987.
Watson et al., *V. International Conference on AIDS*, C632, 663, 1989.
Prabhala et al., *Cancer*, 6:1556–1560, Mar. 15, 1991.
Loya et al., *Arch. Biochem. Phys.*, 293:2, 28–212, Mar., 1992.
Garewal et al., *Symposium: Nutrition, Immunomodulation and AIDS*, 1992.

* cited by examiner

*Primary Examiner*—Russell Travers
(74) *Attorney, Agent, or Firm*—Darby & Darby

(57) ABSTRACT

Methods for raising or maintaining the level of T4 cells in humans having a depressed T4 cell level and particularly in humans infected with HIV are provided. In these embodiments, T4 enhancing amounts of beta-carotene are administered. Methods are also provided for lowering or maintaining the levels of neopterin and/or $\beta_2$-microglobulin in humans having elevated levels of these indices and particularly in those infected with HIV. Beta-carotene is administered, respectively, in neopterin and $\beta_2$-microglobulin therapeutically effective amounts. Also contemplated by the present invention are methods for the prevention and/or treatment of HIV infection in humans. An HIV infection preventing or an anti-HIV therapeutically effective amount of beta-carotene is administered. In another embodiment, methods are provided for preventing or treating AIDS in humans. An AIDS preventing amount or an anti-AIDS therapeutically effective amount of beta-carotene is administered.

14 Claims, No Drawings

BETA-CAROTENE THERAPY OF INDIVIDUALS HAVING ABNORMAL IMMUNOLOGICAL AND SEROLOGICAL INDICES, AND INDIVIDUALS HAVING INFECTIONS AND DISEASES CAUSING CHANGES THEREIN

This is a continuation of application Ser. No. 07/969,485, filed Oct. 30, 1992 now abandoned. The most recent of these prior applications is hereby incorporated herein by reference, in its entirety.

FIELD OF THE INVENTION

The invention relates to a method for (a) the prevention of further deviation from normal levels, (b) the return to normal levels, and/or (c) the maintenance at normal levels of various serological or immunological indices in individuals displaying abnormal levels of these indices. Beta-carotene is administered, preferably systemically, in appropriate amounts. These amounts are higher than those amounts that can be achieved dietarily.

Beta-carotene also produces these effects in individuals susceptible to deviations from normal levels of these indices due to HIV infection or AIDS. Therefore, it is believed that the administration of beta-carotene can be used in the prevention or the treatment of HIV infection or AIDS in humans.

BACKGROUND OF THE INVENTION

The standardized method of evaluating the efficacy of a method of treatment has been to conduct controlled, prospective treatments using clinically relevant endpoints as the main outcome measure. However, in the case of several pathologies such as retroviral infections and diseases, and particularly HIV infection and AIDS, the standard endpoints of death or the development of new AIDS defining opportunistic infections or neoplasms often take months or years to reach. Therefore, several medical and government authorities, including the Federal Drug Administration, have now accepted various laboratory markers which serve as surrogate endpoints for quickly evaluating and establishing the utility of new treatments and particularly anti-retroviral treatments.

Surrogate markers suggested for retroviral infections or diseases, and particularly HIV infection and/or AIDS include, but are not limited to, T4 helper cell levels, neopterin levels and $\beta_2$-microglobulin levels. See, Hutterer et al. J. Infect. Dis. J. 165:783–784, April, 1992; Ellaurie et al. Ped. Infect. Dis. J. 11: 4,286–289, April, 1992; Jacobson et al., Brit. Med. J. 302:73–78, Jan. 12, 1991; Müller et al., Clinica Chimica Acta 201:1–16 (1991); Keller et al., Cells of the Hepatic Sinusoid 3:414–416 (1991); Polis et al., Am. J. Med 89: 701–704, December, 1990; Harrison et al., J. Med Vir. 32:128–133, 1990; Fuchs et al. Clin. Chem. 35:8, 1746–1749, 1989.

Acquired immunodeficiency syndrome (AIDS) is a fatal condition caused by the human immunodeficiency virus (HIV). At least two strains, and possibly more, of HIV have been isolated and identified. HIV-1 is the virus associated with AIDS in most western countries. HIV-2, which is immunounreactively distinct from HIV-1, is associated with AIDS in western Africa.

Since AIDS was identified as a medical condition in 1981, increasing numbers of cases are being reported worldwide, with a large concentration of these cases in the United States. Researchers believe that most carriers of HIV will eventually develop the symptoms of AIDS. However, the period between initial infection by HIV and/or detection of HIV infection and symptomatic AIDS disease is highly variable, as is the rate of immunological decline. The median time between HIV seroconversion and the development of AIDS presently is believed to be about seven to eleven years. Infections by HIV have proven notoriously difficult to treat, and prophylactic or therapeutic vaccines for these infections are presently unavailable and may never be available.

When challenged by retroviral infection, and particularly HIV infection, individuals appear to display one or more of depressed T4 cell levels, elevated neopterin levels, and elevated $\beta_2$-microglobulin levels. Past studies involving the use of beta-carotene in manipulating such endpoints are equivocal at best.

Alexander et al., Immunology Letters 9:221–224, 1985 fed relatively low oral doses of 180 mg/day of beta-carotene for two weeks to normal human volunteers. T4 cells numbers increased up to approximately 30%, but the increase declined to insignificant levels within one week after discontinuing the beta-carotene administration even though a significant elevation in beta-carotene plasma level was still seen six weeks after treatment was discontinued.

However, Ringer et al., Am. J. Clin. Nutr. 53:688–694, 1991, were unable to identify any effects of beta-carotene ingestion on various immunological indices when beta-carotene was administered in dosages of 0, 15, 45, 180 and 300 mg/day for one month to normal, healthy human subjects. Particularly, Ringer et al. did not find an increase in T4 cells at two or four weeks in humans ingesting dosages of beta-carotene ranging from 15 to 300 mg/day.

Kanofsky et al. Med. Trib., 26–31, Apr. 22, 1987 even cautioned that based upon the results of Alexander et al., any immuno-stimulating action of vitamin A or beta-carotene might actually enhance the replication of HIV in HIV-infected individuals. Kanofsky et al. reported the attenuation of the decline of cell-mediated immunocompetence in animals exposed to variables such as trauma, malnutrition, infection, psychological distress, irradiation, cytotoxic agents, and an array of drugs. Particularly, Kanofsky et al. reported providing vitamin A supplementation of approximately 10 to 15 times the recommended dietary allowance of vitamin A to animals exposed to the retrovirus Moloney murine sarcoma virus.

An increased number of activated macrophages and an increased percentage of cells with markers for Ia$^+$ cells and macrophages was associated with a retarded death rate during infection with LP-BM5 murine leukemia in C57BL/6 mice which were fed high dietary vitamin A in a study by Watson et al., Life Sci. 43:XIII–XVIII, 1988. Nashima et al., Med. Microbiol. Immunol., 176:189–198, 1987 reported that, in vitro, the vitamin A derivative, retanoic acid, inhibited the replication of HIV.

In a study of eleven HIV-infected individuals, daily administration of 30 mg of beta-carotene for four months was found to increase the number of cells with natural killer cell activity, IL-2R (interleukin-2 receptors), and transferrin receptors. The reported increase appeared to peak after three months of treatment, and some markers appeared to decline by four months. No significant changes in T-helper (T4), T-suppressor (T8), or total T-cells were observed. Watson et al., V. International Conference on AIDS, C632, 663, 1989.

Prabhala et al., Cancer 6:1556–1560, Mar. 15, 1991, demonstrated that different retinoids and carotenoids have different immunomodulatory effects in the inhibition of malignancies. Different subjects having either oral leukoplakia or Barret's esophagus were given 30 mg/day of beta-carotene or 1 mg/kg/day of 13-cis-retanoic acid (13-cRA). The predominant effect of 13-cRA was on the percentage of cells expressing T-helper markers, while beta-carotene was observed to increase natural killer cell markers. Although T-helper marker expression was increased to a small extent in these cancer patients, no significant changes in total lymphocyte, total T-cell, or T-suppressor cell numbers were reported.

Another carotenoid, halocynthiazanthin, which was isolated from a red sponge from the Gulf of Eilat in the Red Sea, was described as unique among the carotenoids as a specific anti-HIV reverse transcriptase inhibitor by Loyu et al., *Arch. Biochem. Phys.* 293:2,28–212, March, 1992.

Garewal et al., *Symposium: Nutrition, Immunomodulation and AIDS,* 1992 studied the effect of low dosages of beta-carotene on HIV-infected patients. Each subject received 60 mg of beta-carotene daily for four months. Increases in the percentages of cells expressing Leu II (natural killer cells), Ia antigen, and transferrin receptor (activated lymphocytes) were observed after three months of treatment, but diminished thereafter. Major changes were not seen in total lymphocyte count or in the percentage of cells expressing CD11, CD8, or CD4 antigens.

Ozonoids of terpenes, including ozonoids of beta-carotene, have been disclosed for the treatment of viral infections including HIV-infections by Herman, U.S. Pat. Nos. 4,983,637; 5,086,076; and 5,126,376.

It has now been discovered that the administration of beta-carotene in amounts that can not be achieved dietarily and in amounts previously believed to be significantly high, are effective in the therapeutic control and normalization of various immunological and/or serological indices.

SUMMARY OF THE INVENTION

According to the present invention there are provided methods for raising or maintaining the level of T4 cells in humans having a depressed T4 cell level and particularly in humans infected with HIV. In these embodiments, T4 enhancing amounts of beta-carotene are administered.

Methods are also provided for lowering or maintaining the levels of neopterin and/or $\beta_2$-microglobulin in humans having elevated levels of these indices and particularly in those infected with HIV. Beta-carotene is administered, respectively, in neopterin and $\beta_2$-microglobulin therapeutically effective amounts.

Also contemplated by the present invention are methods for the prevention and/or treatment of HIV infection in humans comprising administering to the human, respectively, an HIV infection preventing or an anti-HIV therapeutically effective amount of beta-carotene.

In another embodiment, methods are provided for preventing or treating AIDS in humans comprising administering to the human, respectively, an AIDS preventing amount or an anti-AIDS therapeutically effective amount of beta-carotene.

DETAILED DESCRIPTION OF THE INVENTION

Carotenoids are terpenes that are widely distributed in the plant and animal kingdoms. Beta-carotene is a common carotenoid having the chemical structure:

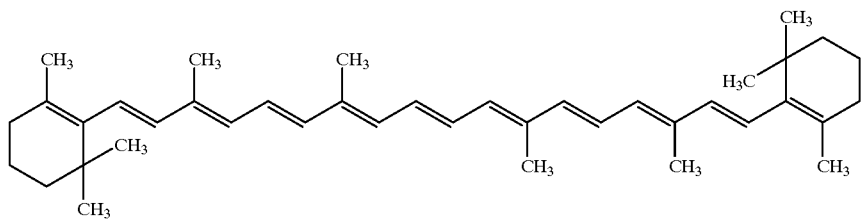

Beta-carotene, in mammals, readily undergoes oxidative cleavage at the central double bond to give two equivalents of the aldehyde retinal. Biochemical reduction of the aldehyde carbon yields vitamin A.

Typically, the T4 cell count in a normal, healthy human adult ranges between about 500 and about 1500. Furthermore, T4 cells comprise from about 35 to about 60 percent of total T cells, i.e. T4 cells and T8 cells, in a normal, healthy adult human. Often, individuals infected with a retrovirus, and particularly with HIV, or individuals afflicted with AIDS have lower than normal T4 cell levels as determined by T4 cell count, percentage of total T cells, or both.

The aspect of the present invention directed to increasing or maintaining T4 cell levels contemplates T4 levels as defined by T4 cell count, percentage of total T-cells, or a combination thereof. Depressed levels of T-cells are those levels below the levels for normal, healthy individuals described above.

Increasing T4 cell levels indicates elevating those levels from any level which is below normal levels, but elevation does not necessarily indicate that those levels are returned to normal levels. Maintaining levels of T4 cells indicates halting any further immunologically, serologically and/or clinically significant decline in T4 cell level from the T4 cell level, whether normal or abnormal but preferably abnormal or abnormally low, of an individual at the commencement of beta-carotene administration. Preferably, T4 cell levels will be maintained for a period of at least about one to about twelve months past any latency period between seroconversion or immunoresponse by any infectious or responsible cause and any ensuing disease. T4 cell levels may fluctuate slightly during maintenance or the period above, but the overall trend will be to maintain these levels at a constant level.

Typically, the neopterin level in a normal, healthy human adult is below about 10 nanomoles, and the $\beta_2$-microglobulin level in a normal, healthy human adult ranges between about 0.7 and about 3.4 mg/l. Often, individuals infected with a retrovirus, and particularly with HIV, or individuals afflicted with AIDS have higher than normal neopterin and/or $\beta_2$-microglobulin.

Elevated levels of neopterin and/or $\beta_2$-microglobulin are those levels above the levels for normal, healthy individuals described above. Lowering neopterin and/or $\beta_2$-microglobulin levels indicates lowering these levels from any levels which are above normal levels, but lowering does not necessarily indicate that those levels are returned to normal levels.

Maintaining levels of neopterin and/or $\beta_2$-microglobulin indicates halting any further immunologically, serologically, and/or clinically significant elevation of neopterin and/or $\beta_2$-microglobulin levels from the neopterin and/or $\beta_2$-microglobulin levels, whether normal or abnormal but preferably abnormal or abnormally high, of an individual at the commencement of beta-carotene administration. Preferably, neopterin levels and/or β2-microglobulin levels will be maintained for a period of at least about one to about twelve months past any latency period between seroconversion or immunoresponse by any infectious or responsible cause and any ensuing disease. Neopterin and/or $\beta_2$-microglobulin levels may fluctuate slightly during maintenance or these periods, but the overall trend will be to maintain these levels at a statistically constant level. Typically, $\beta_2$-microglobulin levels will fluctuate to a greater degree during maintenance than will neopterin levels.

HIV, as used herein, is meant to encompass HIV-1, HIV-2, and any other HIV strains which are associated with AIDS or similar diseases. Because HIV is a retrovirus, it is possible that further HIV variants will be identified and/or isolated. It is further believed that the methods of the present invention will be useful in the treatment of infection by or disease due to all such strains, and confirmation of this is within the ordinary skill of those in the art by known testing methods. The term HIV infection refers to infection by HIV as defined above.

In all of the embodiments of the present invention, beta-carotene is preferably administered systemically. Systemic administration, most preferably, is by the oral route.

A daily dosage identifies the average amount of beta-carotene administered to an individual. Although the daily dosage may actually be administered daily, it need not be administered daily. The daily dosage is merely an average dosage that an individual receives when beta-carotene is administered over a period of time. The daily dosage can be administered in divided portions so that the total amount administered is the daily dosage.

Beta-carotene is a component of a normal human diet, and the recommended daily requirement of beta-carotene for a normal adult human is about 3 mg. Although beta-carotene is provided through normal diet, the amounts of beta-carotene useful in the present invention typically can not be provided by normal diet. This is because the foods that supply beta-carotene in the normal diet contain various other substances. If sufficient amounts of these foods were consumed to provide the necessary amounts of beta-carotene, these other substances would be consumed in toxic amounts. Furthermore, approximately 25–75 percent of the carotenoids consumed in a normal diet are not absorbed and are excreted in the feces relatively unchanged. Therefore, beta-carotene is supplied in the methods of the present invention through supplementation. Commercially available forms of beta-carotene are available, for example, from Hoffman-LaRoche under the trademark SOLATENE™ or as "beta-carotene".

The amounts of beta-carotene useful for raising or maintaining the level of T4 cells in a human having a depressed level of T4 cells, and particularly wherein the depression is due to retroviral infection, HIV infection, or AIDS, is a T4 cell enhancing amount. T-4 cell enhancing amounts will depend independently upon the age, weight, sex, sensitivity, medical condition, including, but not limited to, the stage of infection or disease, and the like of the individual, but will be a safe, non-toxic amount. These amounts can be determined by experimentation well known in the art such as by establishing a matrix of dosages and frequencies and assigning a group of experimental subjects to each point in the matrix.

Although the safe, non-toxic upper limit of the amount of beta-carotene that can be administered to a human has not yet been determined, it is believed that such an upper limit is at least 1000 mg/day.

Typically, for an adult human, a T4 cell enhancing amount of beta-carotene is at least about 250 mg/day. Preferably, this amount will be at least about 300 mg/day, 350 mg/day, 400 mg/day or 500 mg/day.

The amounts of beta-carotene useful for lowering or maintaining the level of neopterin or $\beta_2$-microglobulin in a human having elevated levels of neopterin and/or $\beta_2$-microglobulin, and particularly wherein the elevation is due to retroviral infection, HIV infection, or AIDS, are neopterin therapeutically effective levels of beta-carotene and $\beta_2$-microglobulin therapeutically effective levels of beta-carotene, respectively. These amounts depend independently upon the age, weight, sex, sensitivity, medical condition, including, but not limited to, the stage of infection or disease, and the like of the individual, but can be determined as above.

Typically for an adult human, these amounts will be safe, non-toxic amounts and preferably will be at least about 250 mg/day. Most preferably, the amounts independently will be at least 300 mg/day, 350 mg/day, 400 mg/day, or 500 mg/day.

The amounts of beta-carotene required to prevent or to treat HIV infection are HIV infection preventing amounts or therapeutically effective amounts of beta-carotene, respectively. Anti-HIV therapeutically effective amounts are those amounts of beta-carotene sufficient to stabilize the progression or the intensity of HIV infection or to resolve the symptoms of HIV infection. HIV infection preventing amounts or anti-HIV therapeutically effective amounts of beta-carotene also will depend independently upon the age, weight, sex, sensitivity, medical condition including, but not limited to, the stage of infection or disease, and the like of the individual. These amounts can be determined as above.

Typically for an adult human, these amounts will be safe, non-toxic amounts and preferably, at least about 250 mg/day. Most preferably, these amounts independently will be at least about 300 mg/day, 350 mg/day, 400 mg/day or 500 mg/day.

The amounts of beta-carotene required to prevent or to treat AIDS are AIDS preventing amounts or anti-AIDS therapeutically effective amounts of beta-carotene, respectively. Anti-AIDS therapeutically effective amounts are those amounts of beta-carotene sufficient to stabilize or to resolve the progression and/or the intensity of AIDS, to forestall or to prevent further opportunistic infections or malignancies, or to reduce or to resolve any or all of the symptoms of AIDS present at the commencement of beta-carotene administration. Again, the amounts will depend independently upon the age, weight, sex, sensitivity, medical condition, including, but not limited to, the stage of infection or disease, and the like of the individual, but can be determined as detailed above.

Typically for an adult human, these amounts will be safe non-toxic amounts and preferably at least about 250 mg/day.

Most preferably, these amounts independently will be 300 mg/day, 400 mg/day or 500 mg/day.

Beta-carotene administration in any of the methods of the present invention can be accompanied by the administration of an adjuvant such as a beta-carotene absorption enhancing adjuvant including, but not limited to, safflower oil, bile salts, lipids, proteins, antioxidants, zinc or any combination thereof. Typically, between about 2 and 20 grams/day, preferably between about 10 and 20 grams/day, and most preferably between about 12 and 16 grams/day of safflower oil will be used as an adjuvant. Adjuvant administration can proceed, be concurrent with, follow, or any combination thereof, beta-carotene administration.

Furthermore, beta-carotene administration can accompany the administration of other therapeutics that may be used in the treatment or prevention of any retroviral infection or disease. For example, in the prevention or treatment of HIV infection or AIDS, beta-carotene administration can proceed, be concurrent with, follow, or any combination thereof, the administration of agents commonly used for that purpose and well known in the art such as AZT, DDI, DDC, and/or 4DT. Beta-carotene administration pursuant to the present invention should not interfere with the anti-retroviral effects of such agents and indeed may allow for the effective administration of lower or higher amounts of these agents for disease treatment. This is an important alternative embodiment of the present invention because these agents have substantial toxicity which can result in ineffectiveness or necessitate discontinuance of their use or non-compliance in certain patients.

Because of the minimal side effects of beta-carotene, beta-carotene administration can continue for extended periods of time, and even for the lifetime of the individual, in order to maintain any immunological, serological, prophylactic, or therapeutic effects. Any increase in T4 cell levels or decrease in neopterin or $\beta_2$-microglobulin levels pursuant to the use of beta-carotene as set forth herein is within the scope of the present invention.

DESCRIPTION OF THE PREFERRED EMBODIMENTS

The following examples illustrate the invention without limitation.

EXAMPLE 1

An individual having a below normal T4 cell level, and above normal neopterin and $\beta_2$-microglobulin levels is administered 300 mg/day of beta-carotene orally for a period of six weeks. T4 cell level is increased, neopterin level is decreased, and $\beta_2$-microglobulin level is decreased.

EXAMPLE 2

Normal healthy individuals at an increased risk for HIV infection (hemophiliacs, intravenous drug users, and homosexual men) are administered 300 mg/day of beta-carotene orally for a period of three months to 1 year. The individuals are monitored for HIV infection and alterations in T4 cell levels and neopterin and $\beta_2$-microglobulin levels. It is expected that beta-carotene administration will prevent HIV infection in these individuals.

An antibody test indicates the absence of HIV infection.

The above mentioned patents, test methods, and publications are hereby incorporated by reference in their entirety.

Many variations of the present invention will suggest themselves to those skilled in the art in light of the above detailed description. For example, beta-carotene can be administered to prevent or to treat other retroviral infections or diseases or diseases of unexplained origin which affect T4 cell levels such as idiopathic CD4+ T-lymphocytopenia. Additionally, beta-carotene may be added to whole blood or blood components to remove or to inactivate retroviruses including, but not limited to, HIV in order to purify blood and render it safe for transfusion. All such obvious variations are within the full intended scope of the appended claims.

In the claims:

1. A method for lowering or maintaining the level of neopterin in a human having an elevated level of neopterin, said method comprising administering to said human a neopterin therapeutically effective amount of beta-carotene.

2. A method as defined in claim 1, wherein said neopterin therapeutically effective amount of beta-carotene comprises at least about 250 mg/day.

3. A method as defined in claim 2, wherein said neopterin therapeutically effective amount of beta-carotene comprises at least about 300 mg/day.

4. A method as defined in claim 1, wherein said administering is systemic.

5. A method as defined in claim 4, wherein said administering is oral.

6. A method as defined in claim 1, wherein said neopterin elevation is due to HIV infection.

7. A method for lowering or maintaining the level of neopterin in a human infected with HIV, said method comprising administering to said human a neopterin therapeutically effective amount of beta-carotene.

8. A method for lowering or maintaining the level of $\beta_2$-microglobulin in a human having an elevated level of $\beta_2$-microglobulin, said method comprising administering to said human a $\beta_2$-microglobulin therapeutically effective amount of beta-carotene.

9. A method as defined in claim 8, wherein said $\beta_2$-microglobulin therapeutically effective amount of beta-carotene comprises at least about 250 mg/day.

10. A method as defined in claim 9, wherein said $\beta_2$-microglobulin therapeutically effective amount of beta-carotene comprises at least about 300 mg/day.

11. A method as defined in claim 8, wherein said administering is systemic.

12. A method as defined in claim 11, wherein said administering is oral.

13. A method as defined in claim 8, wherein said $\beta_2$-microglobulin elevation is due to HIV infection.

14. A method for lowering or maintaining the level of $\beta_2$-microglobulin in a human infected with HIV, said method comprising administering to said human a $\beta_2$-microglobulin therapeutically effective amount of beta-carotene.

* * * * *